US010773079B2

(12) United States Patent
Keller et al.

(10) Patent No.: US 10,773,079 B2
(45) Date of Patent: Sep. 15, 2020

(54) SYSTEM AND METHOD FOR FUNCTIONAL ELECTRICAL STIMULATION

(71) Applicant: FESIA TECHNOLOGY, S.L., Donosita (Gipuzkoa) (ES)

(72) Inventors: Thierry Keller, Derio (ES); Nebojsa Malesevic, Belgrado (RS); Goran Bijelic, Belgrado (RS)

(73) Assignee: FESIA TECHNOLOGY, S.L., Donostia (Gipuzkoa) (ES)

( * ) Notice: Subject to any disclaimer, the term of this patent is extended or adjusted under 35 U.S.C. 154(b) by 0 days.

(21) Appl. No.: 15/318,298

(22) PCT Filed: Jun. 13, 2014

(86) PCT No.: PCT/EP2014/062474
§ 371 (c)(1),
(2) Date: Dec. 12, 2016

(87) PCT Pub. No.: WO2015/188889
PCT Pub. Date: Dec. 17, 2015

(65) Prior Publication Data
US 2017/0106189 A1 Apr. 20, 2017

(51) Int. Cl.
*A61N 1/05* (2006.01)
*A61N 1/36* (2006.01)
*A61N 1/04* (2006.01)

(52) U.S. Cl.
CPC ....... *A61N 1/36003* (2013.01); *A61N 1/0452* (2013.01); *A61N 1/0456* (2013.01);
(Continued)

(58) Field of Classification Search
CPC ............ A61N 1/36003; A61N 1/36014; A61N 1/0452; A61N 1/0484
See application file for complete search history.

(56) References Cited

U.S. PATENT DOCUMENTS 5,643,332 A 7/1997 Stein
10,086,196 B2 * 10/2018 Glukhovsky ...... A61N 1/36003
(Continued)

OTHER PUBLICATIONS

European Patent Office Searching Authority, PCT International Search Report, PCT/EP2014/062474, dated Oct. 24, 2014, 5 pages.

*Primary Examiner* — Michael J D Abreu

(57) ABSTRACT

A functional electrical stimulation system (1) for correction of drop-foot, comprising: a device (3) to be placed on a paretic leg, provided with a plurality of multi-pad electrodes (315) on one side (31), at least one of said electrodes (315) being configured to provide a stimulating electric signal on the point of the leg on which it is positioned, wherein said corresponding stimulating electric signals form a stimulation pattern; and at least one sensor (8) to be positioned on either said leg or corresponding foot, the sensor (8) being configured to, measure information during movement and emit sensor signals indicative thereof. The system further comprises means (6) for calculating a foot trajectory from said sensor signals, for detecting gait phase from said foot trajectory, for evaluating the quality of gait from said foot trajectory and for, if the quality of gait is below a certain threshold, modifying said stimulation pattern; and means (7) for selectively activating at least one of said electrodes (315) according to said modified stimulation pattern. Method, use and computer program product.

8 Claims, 10 Drawing Sheets

(52) U.S. Cl.
CPC ......... *A61N 1/0476* (2013.01); *A61N 1/0484* (2013.01); *A61N 1/0492* (2013.01); *A61N 1/36014* (2013.01)

(56) References Cited

U.S. PATENT DOCUMENTS

| | | | |
|---|---|---|---|
| 2007/0179561 A1* | 8/2007 | Embrey | A61N 1/36003 607/49 |
| 2011/0137375 A1 | 6/2011 | McBride | |
| 2012/0059432 A1* | 3/2012 | Emborg | A61N 1/36003 607/49 |
| 2015/0100104 A1* | 4/2015 | Kiani | A61N 1/36003 607/49 |

* cited by examiner

| Step | Stimulation pattern | P table | |
|---|---|---|---|
| 0 | ... 0 0 0 0 0 0 16 0 ...<br>... 0 0 0 0 0 0 16 0 ... | ... 0 0 0 2 4 14 20 10 ...<br>... 0 0 0 1 5 15 18 11 ... | Qd=32 |
| 1 | ... 0 0 0 0 0 0 18 0 ...<br>... 0 0 0 0 0 0 18 0 ... | ... 0 0 0 2 4 15 19 10 ...<br>... 0 0 0 1 5 16 17 11 ... | Qd=35 |
| 2 | ... 0 0 0 0 0 0 20 0 ...<br>... 0 0 0 0 0 0 20 0 ... | ... 0 0 0 2 4 15 19 10 ...<br>... 0 0 0 1 5 17 16 11 ... | Qd=36 |
| 3 | ... 0 0 0 0 0 0 18 0 ...<br>... 0 0 0 0 0 16 18 0 ... | ... 0 0 0 2 4 15 19 10 ...<br>... 0 0 0 1 5 18 15 11 ... | Qd=48 |
| 4 | ... 0 0 0 0 0 0 18 0 ...<br>... 0 0 0 0 0 18 16 0 ... | ... 0 0 0 2 5 16 18 8 ...<br>... 0 0 0 1 7 22 12 9 ... | Qd=58 |
| 5 | ... 0 0 0 0 0 14 16 0 ...<br>... 0 0 0 0 0 22 0 0 ... | ... 0 0 0 2 5 17 17 7 ...<br>... 0 0 0 1 8 23 11 9 ... | Qd=70 |

FIG. 11

SYSTEM AND METHOD FOR FUNCTIONAL ELECTRICAL STIMULATION

TECHNICAL FIELD

The present invention relates to the field of functional electrical stimulation (FES) devices and, in particular, to FES devices and methods for treating drop-foot disorders.

STATE OF THE ART

Drop-foot, also called foot drop, refers to the inability or difficulty in moving the ankle and toes upward while walking. In other words, it refers to the difficulty in lifting the front part of the foot. It is not a disease itself: it is often a proof of an underlying neurological disorder (stroke, spinal cord injury, cerebral palsy, or peripheral injury). Depending on the severity of drop-foot, its consequences range from unaesthetic walking and increased energy expenditure to an increased risk of falling or even the complete inability to walk. It can be either temporary or permanent.

Drop-foot is a result of an interruption or severance of the communication path between the brain, motor nerves and leg muscles. The actual reason of drop-foot is that the spinal brain is not operating as it should because of pathway leasions, modified central input and modified afferent signals. Traditionally, drop-foot treatment devices were limited to accommodative devices that prevent the dragging of the toes. The ankle foot orthosis (AFO) functions by limiting the speed at which the foot plantar flexes during the loading response (foot slap) and prevents the foot from dropping during the swing phase of gait (drop foot). This prevents the toe of the foot from coming in contact with the floor and decreases the risk of stumbling. The AFO typically extends from distal to the metatarsal heads to just distal to the head of the fibula.

In recent years drop-foot has been commonly treated by means of functional electrical stimulation (FES) devices. FES devices activate motoneurons or reflex pathways by electrically stimulating nerve fibers. For example, international patent application WO2011/079866A1 discloses an apparatus for external activation of paralyzed body parts by stimulation of peripheral nerves or muscles, which comprises a soft apparel provided with multi-pad electrodes on one side and activating means on the other side. In the context of drop-foot, the use of FES devices enables patients to lift their foot (toes) periodically as part of a close to natural gait cycle.

Today both transcutaneous and implantable systems are available. Commonly, transcutaneous FES systems are used both in rehabilitation and as an orthosis, while implantable FES systems are only orthotic. A patient is considered to be a good candidate for implantation of a FES system if the transcutaneous FES therapy did not lead to satisfactory level of rehabilitation while the usage of surface FES orthosis successfully reconstructs the lost function. Disadvantages related to possible problems with the long-term implantation and long-term changes due to the stimulation (e.g. irreversible deleterious effects to the neural tissue or physical failure of an electrode, which requires an invasive revision procedure) along with surgery risks, make people lean towards surface devices rather than towards implants.

The advantage of systems based on surface electrodes is that they can be applied in early stages after stroke as additional therapy procedure. There is growing evidence that electrical stimulation contributes to better recovery and has long term effects since it does more than bringing the foot up during the swing: it activates many afferent fibers and provides a strong input to the central nervous system. It has been shown in clinical studies that FES combined with exercise significantly increases the carry-over effects of therapy compared to therapies based only on exercise.

United States patent application US2007/0112394A1 describes a functional electrical stimulation orthosis for providing functional electrical stimulation to a limb segment of a user. A product implemented according to such disclosure is the NESS L300®, owned by Bioness Inc. It is light-weight, fits just below the knee and is designed to be easy to put on and take off. It has three main parts: a leg cuff, a gait sensor and a remote control that use wireless communication. Stimulation pulses are delivered to the skin by commercial self-adhesive electrodes and timing is produced by a pressure heel switch. A trained clinician does initial adjustments of electrode positioning and stimulation parameters, while the user has control of some parameters via the remote control unit.

United States patent applications U.S. Pat. No. 5,643,332A and U.S. Pat. No. 5,814,093A describe a functional electrical stimulator. A product implemented according to such disclosure is the WalkAide drop-foot stimulator owned by Innovative Neurotronics Inc. It is a battery-operated, single-channel electrical stimulator that utilizes a tilt sensor to control the activation and deactivation of the stimulation during normal gait. It comprises an integrated single-channel electrical stimulator, two electrodes and electrode leads. The WalkAide can effectively counteract foot drop by producing dorsiflexion of the ankle during the swing phase of the gait. The device is attached to the leg, just below the knee, near the head of the fibula. The user can adjust intensity.

The device shown in U.S. Pat. No. 5,643,332A only measures the orientation of the leg shank, but not the orientation of the foot. It therefore cannot control the position of the foot. It is limited to modify on/off timing of the stimuli and no other stimulation parameters: The system only adjusts the timing of the stimulation (ON/OFF) and not the intensity or any other stimulation parameter dependent on the angle of the shank with respect to gravity.

In sum, none of the disclosed devices are capable of adjusting in real-time the stimulation electrodes or the stimulation parameters, such that an optimal movement is obtained.

DESCRIPTION OF THE INVENTION

It is therefore an object of the invention to provide a functional electrical stimulation device and method for correction of drop-foot which has the ability to adapt during use, thus optimizing its performance.

According to an aspect of the present invention, there is provided a functional electrical stimulation system for correction of drop-foot, comprising: a device configured to be placed on a paretic/affected leg of a user, the device being provided with a plurality of multi-pad electrodes on one side, wherein at least one of the electrodes is configured to provide a stimulating electric signal on the point of the leg on which it is positioned, wherein the corresponding stimulating electric signals form a stimulation pattern; and at least one sensor configured to be positioned on either the paretic/affected leg or corresponding foot of the user during use of the system. The sensor is configured to, in use of the system, measure information during movement and emit sensor signals indicative thereof. The system further comprises means for calculating a foot trajectory from the sensor signals, for detecting gait phase from the foot trajectory, for evaluating the quality of gait from the foot trajectory and for, if the quality of gait is below a certain threshold, modifying the stimulation pattern; and means for selectively activating at least one of the electrodes according to the modified stimulation pattern.

In a preferred embodiment, the means for evaluating the quality of gait from the foot trajectory further comprises means for loading a predefined trajectory and for calculating the deviation of a current step from the predefined trajectory. Also preferably, the quality of gait is evaluated when the gait is in the following phases: during plantar flexion in the push-off gait phase and in the dorsiflexion in swing gait phase when the user is clearing the foot from the ground.

The means for selectively activating at least one of the electrodes according to the modified stimulation pattern comprises multiplexor means for discrete activation or deactivation of electrodes and for adjusting at least one of the following parameters associated to each electrode: the amplitude of the pulse, the width of the pulse and the time delay between consecutive electrode activations.

In a preferred embodiment, the system comprises a garment to which the device is attached.

Preferably, the sensor comprises means for obtaining its own orientation based on the moments of stance of gait during which the sensor is stationary. More preferably, the means for obtaining the sensor own orientation comprises a plurality of accelerometers and a plurality of gyroscopes.

In a particular embodiment, the means for calculating a foot trajectory from the sensor signals, for detecting gait phase from the foot trajectory, for evaluating the quality of gait from the foot trajectory and for, if the quality of gait is below a certain threshold, modifying the stimulation pattern, are at least partially located in the sensor.

In another particular embodiment, the means for calculating a foot trajectory from the sensor signals, for detecting gait phase from the foot trajectory, for evaluating the quality of gait from the foot trajectory and for, if the quality of gait is below a certain threshold, modifying the stimulation pattern, are at least partially located in a housing located on the user's paretic/affected leg.

In a particular embodiment, the system comprises means for wirelessly sending data obtained, preprocessed or processed at the sensor to processing means placed in a different location.

In another aspect of the invention, it is provided a method for correction of drop-foot based on functional electrical stimulation. The method comprises: applying a stimulation pattern on a paretic/affected leg of a user my means of a plurality of multi-pad electrodes, each of them being configured to provide a stimulating electric signal on the point of the leg on which it is positioned; measuring information during movement and emitting sensor signals indicative thereof; calculating a foot trajectory from the sensor signals; detecting gait phase from the foot trajectory; evaluating the quality of gait from the foot trajectory; if the quality of gait is below a certain threshold, modifying the stimulation pattern, and selectively activating at least one of the electrodes according to the modified stimulation pattern.

In a preferred embodiment, the gait phase detection comprises detecting the end of swing starting point and the end point of swing, wherein the end of swing starting point is determined as the half of the maximum velocity during swing phase and wherein the end point of swing is the heel strike, which corresponds to the crossing of positive angular velocity to negative values.

Preferably, the quality of gait evaluation further comprises loading a predefined trajectory and calculating the deviation of a current step from the predefined trajectory.

The quality of gait is preferably evaluated when the gait is in the following phases: during plantar flexion in the push-off gait phase and in the dorsiflexion in swing gait phase when the user is clearing the foot from the ground.

The modification of the stimulation pattern preferably comprises the discrete activation or deactivation of electrodes and the adjustment of at least one of the following parameters associated to each electrode: the amplitude of the pulse, the width of the pulse and the time delay between consecutive electrode activations.

In another aspect of the invention, it is provided the use of the system previously described, in the treatment of drop-foot.

In a final aspect of the invention, it is provided a computer program product comprising computer program instructions/code for performing the method previously described.

Additional advantages and features of the invention will become apparent from the detail description that follows and will be particularly pointed out in the appended claims.

BRIEF DESCRIPTION OF THE DRAWINGS

To complete the description and in order to provide for a better understanding of the invention, a set of drawings is provided. Said drawings form an integral part of the description and illustrate an embodiment of the invention, which should not be interpreted as restricting the scope of the invention, but just as an example of how the invention can be carried out. The drawings comprise the following figures:

FIG. 11 illustrates the algorithm for the modification of the stimulation pattern for defining the electrical stimuli to be applied to an array of electrodes.

DESCRIPTION OF A WAY OF CARRYING OUT THE INVENTION

In this text, the term "comprises" and its derivations (such as "comprising", etc.) should not be understood in an excluding sense, that is, these terms should not be interpreted as excluding the possibility that what is described and defined may include further elements, steps, etc.

In the context of the present invention, the term "approximately" and terms of its family (such as "approximate", etc.) should be understood as indicating values very near to those which accompany the aforementioned term. That is to say, a deviation within reasonable limits from an exact value should be accepted, because a skilled person in the art will understand that such a deviation from the values indicated is inevitable due to measurement inaccuracies, etc. The same applies to the terms "about", "around", "close to" and "substantially".

The following description is not to be taken in a limiting sense but is given solely for the purpose of describing the broad principles of the invention. Next embodiments of the invention will be described by way of examples, with reference to the above-mentioned drawings showing apparatuses and results according to the invention.

Figure 1:
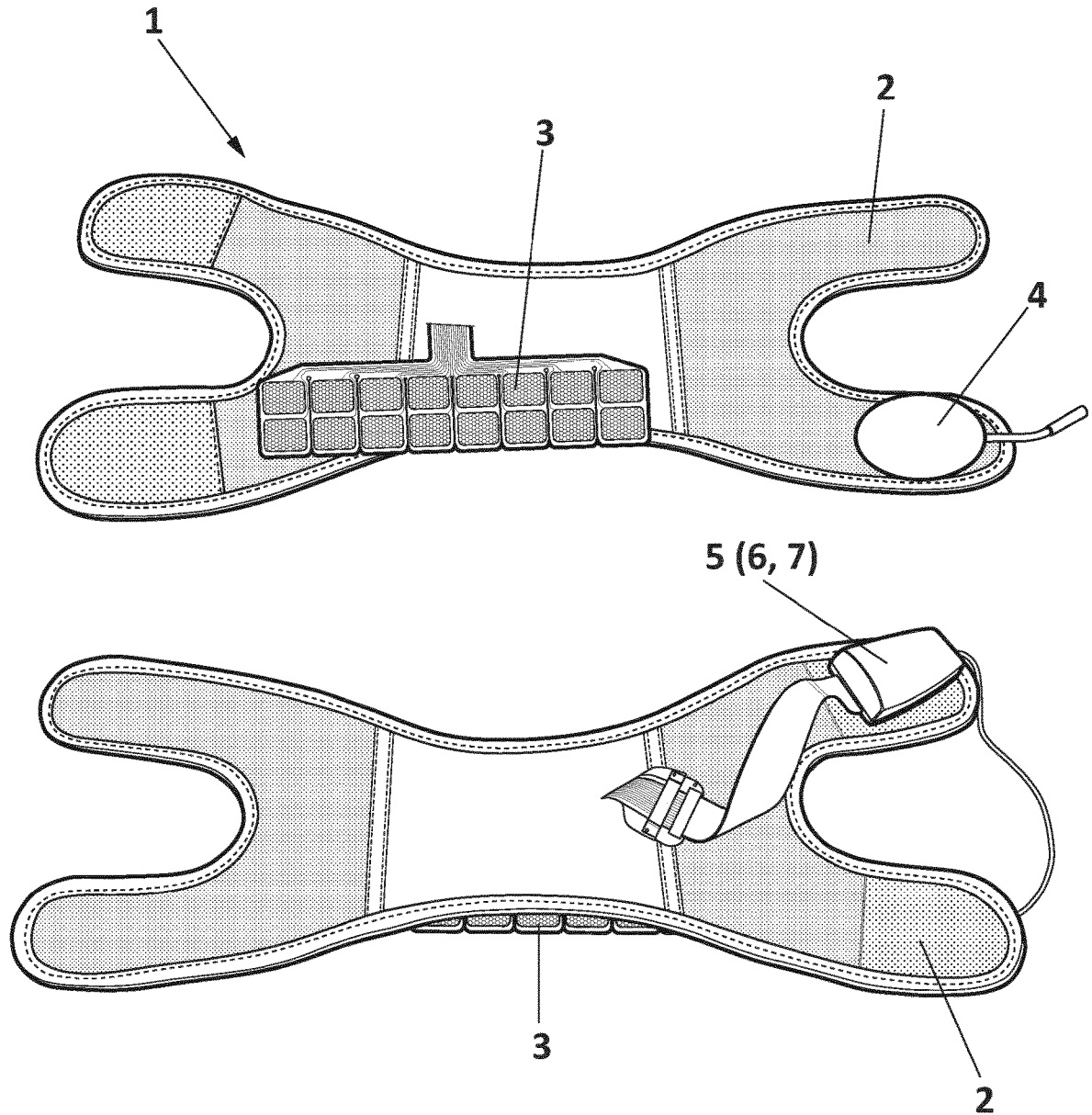
FIG. 1 shows a system 1 for correction of drop-foot according to an embodiment of the invention.

FIG. 1 shows a FES system 1 for correction of drop-foot according to an embodiment of the invention. The illustrated system 1 comprises a garment 2 designed to be placed on a leg of a user suffering from drop-foot. In FIG. 1, the upper view shows the inner part of the garment 2, that is to say, the part designed to be in contact with the user's leg. This part has an array of electrodes (electrode pads). The lower view shows the outer part of the garment 2, that is to say, the visible part when a user is wearing the garment 2. The garment 2 is preferably placed on the patient's knee with the array of electrodes positioned on the Popliteal Fossa. A housing 5 is integrated into the garment, preferably on its outer side. The housing 5 has processing means (also referred to as control means). The processing means, control means or control unit can be totally or partially located at the housing 5. This control means can have stimulation and signal processing unit 6 (also referred to as a stimulator 6 or stimulating means). Alternatively, the stimulation and signal processing unit 6 can be at least partially integrated in a sensor 8 (for example in a microprocessor) not shown in FIG. 1. The sensor 8 is explained later in this description. The housing 5 is attached to the garment with a clipping mechanism that connects the control means to the electrode pads and establishes electrical contact to a demultiplexor 7 that distributes the stimulation pulses to the pads. The demultiplexor 7 is preferably located within the housing 5. The demultiplexor 7 is controlled by the processing unit 6 and activates a selection of pads to be active, depending on the quality of gait, as will be described later in this text. The stimulation and signal processing unit 6 and the demultiplexor 7 can be integrated within a single housing 5, as depicted in FIG. 1. It is remarked that reference 5 is used to refer both to the hardware (housing) and to the software means (control means) comprised within said hardware. In FIG. 1 the attaching mechanism is a clipping mechanism. Other well-known attaching mechanisms can alternatively be used.

Figure 2:
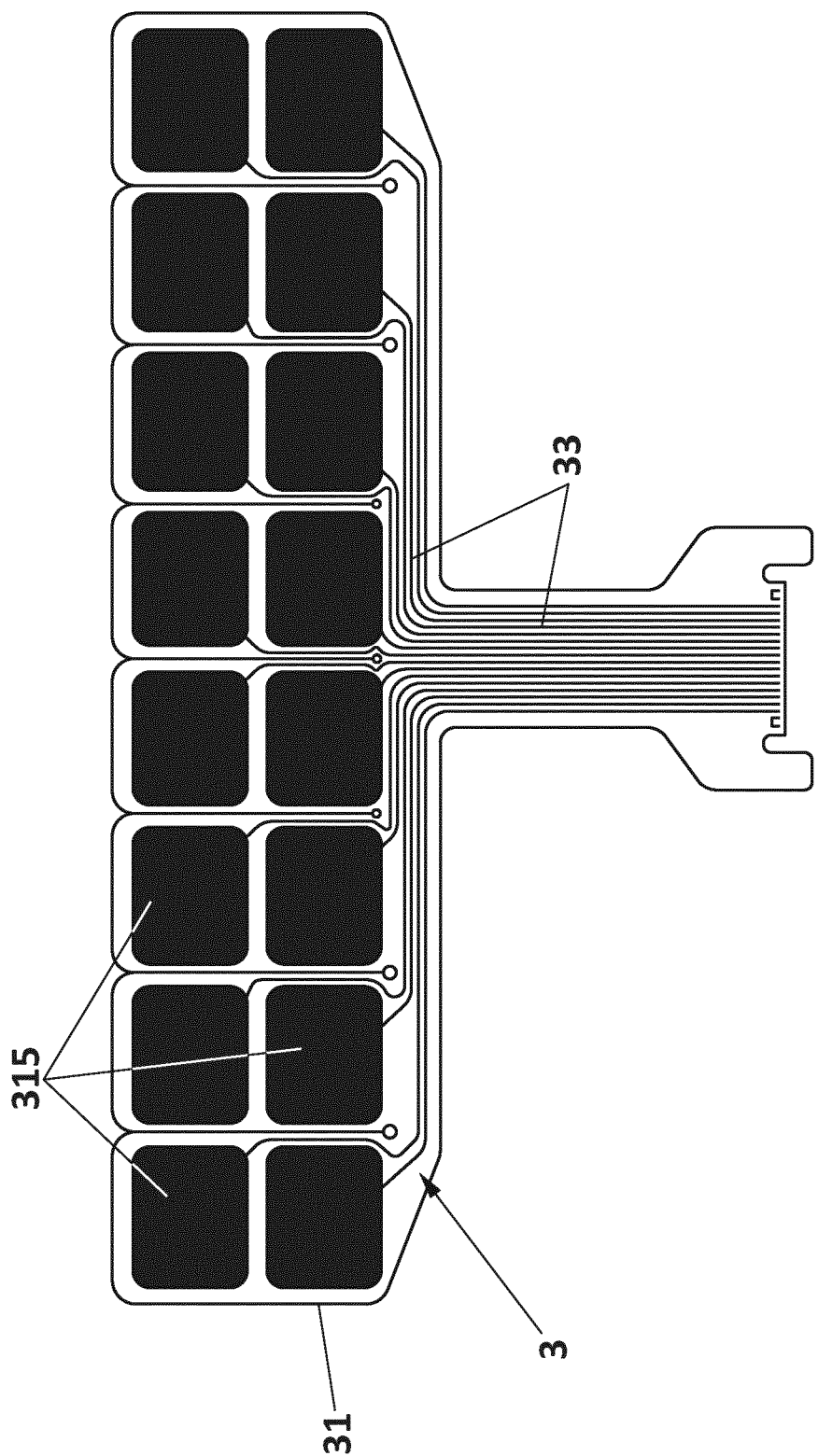
FIG. 2 shows an exemplary device with integrated stimulator and array electrodes according to the invention. The device has a layer of multi-pad electrodes configured to be in contact with the skin and a layer of activating points.

The garment 2 has a device 3 attached or integrated thereto, with integrated stimulator and array of electrodes. The device 3 is formed by at least one layer, as illustrated in FIG. 2. The device 3 has a stimulation layer 31 formed by a plurality of multi-pad electrodes 315 configured to be in contact with the skin. As shown in FIG. 1, this device 3 is placed in the inner surface of the garment 2, so that in use, the multi-pad electrodes 315 are in contact with the user's skin. The electrodes 315 also have connectors 33 for connecting the electrodes 315 to the demultiplexer 7, which comprises analog switches, such as analog optocouplers.

The garment 2 is made of any skin-friendly material. Non-limiting examples of such materials are soft Neoprene, Nylon, polyurethane, polyester, polyamide, polypropylene, silicone, cotton or any other material which is soft and flexible. All named materials could be used as woven, non-woven, single use fabric or laminated structures.

The multi-pad electrodes 315 are small enough to allow controlled (spatial and temporal) current flow between the anode and cathode. The location of the cathode (this is the electrode that depolarizes the excitable tissue, e.g. motor nerves) on the body determines where muscles or nerves are activated; in this case, the muscles or nerves are the ones implied in the drop-foot. The anode can be located at any position of the same body and is often referred to as indifferent electrode. FIG. 1 shows the anode 4 in the embodied FES system 1. It is embedded in or attached to the garment and configured to be placed below the Meniscus in use of the system. This preferred position has been determined in order to minimize the interference with movement and sensation produced by the multi-pad electrode. The active surface area of the anode 4 is preferably bigger than that of the individual cathode pads 315 in order to decrease current density under it, thus being less probable that nerves under the anode become activated. With a slightly different implementation of the demultiplexer, however any of the electrode pads 315 can be used as anode or cathode leaving the flexibility of selecting both the locations of anodes and cathodes. The layer 31 of multi-pad electrodes 315 used as cathode can selectively direct the electric current needed to depolarize the nerve and therefore stimulate the activation of peripheral nerves, based on an algorithm which is explained next. Such selective activation postpones fatigue, which is typical for electrical stimulation with surface electrodes with conventional devices. It can also adapt to changes of the stimulated nerve location with respect to the skin and the multi-pad electrode, which is a common phenomenon due to dynamic changes of the limb configuration during gait, but also due to slower changes of e.g. limb diameter occurring from changes in hydration and vascularization or temporal swelling of the limb.

The stimulation and signal processing unit 6 can communicate through a wireless protocol with external devices, such as smartphones, tablets or PCs comprising a user application. The user application is optional. It can provide indicators and controls of the stimulation process. Through a wireless connection, the user or therapist can set specific stimulation parameters, initiate stimulation protocols (which are running on stimulator processor) and observe stimulation execution. The stimulator 6 is responsible for the real-time control and delivery of stimulation based on control algorithms stored in a stimulator memory and executed in processing means upon user request. Through the stimulator 6, the device can be turned on and off, and some parameters like the overall stimulation intensity can be adjusted. The stimulation demultiplexer 7 is an electronic component designed for efficient stimulation pulses steering to designate stimulation areas (the electrode pad).

In a particular embodiment, not illustrated in FIG. 2, the multi-pad electrode 315 can be manually controlled by a user, thus permitting manual adjustments. In this embodiment, the device 3 additionally comprises a layer comprising sensing pads (also called activating means, activating points or activation sensors). This additional layer is situated on the surface of the device 3 opposite to the surface on which the multi-pad electrodes 315 are placed. The activating points are configured to selectively activate/deactivate a corresponding electrode of the multi-pad electrode. The manual activation of electrodes is preferably used in combination with external devices via wireless communication.

The device 3 can adopt any shape, as long as it comprises at least one electrode (cathode). In the case in which no separate anode is implemented, the minimal configuration of the device 3 comprises at least two electrodes (one anode and one cathode). FIG. 2 shows a preferred multi-pad electrode design having a matrix of two rows of electrodes or pads 315, each row having eight elements. The best response of either a single or a multiple set of pads, which are activated all at the same time (synchronous case) or consecutively (one pad after another) in an asynchronous case is evaluated. In this embodiment, the contacts are rectangular with rounded edges to minimize so-called edge-effects (high current densities at the electrode edges). Other arbitrary shapes and number of pads could be utilized instead. The size and shape of the pads are chosen so as to produce comfortable but also selective stimulation. The layer 31 with multi-pad electrodes 315 are preferably integrated into the soft and flexible substrate (garment 2), that is designed in a manner which allows positioning of the system in just one possible way; thereby facilitating the application of the system. The garment 2 is made in such a way that it takes into account leg landmarks (knee meniscus) for simple and repeatable repositioning with acceptable tolerance (about ±2 cm). The repositioning error is compensated by adjusting the stimulation pattern.

Figure 3:
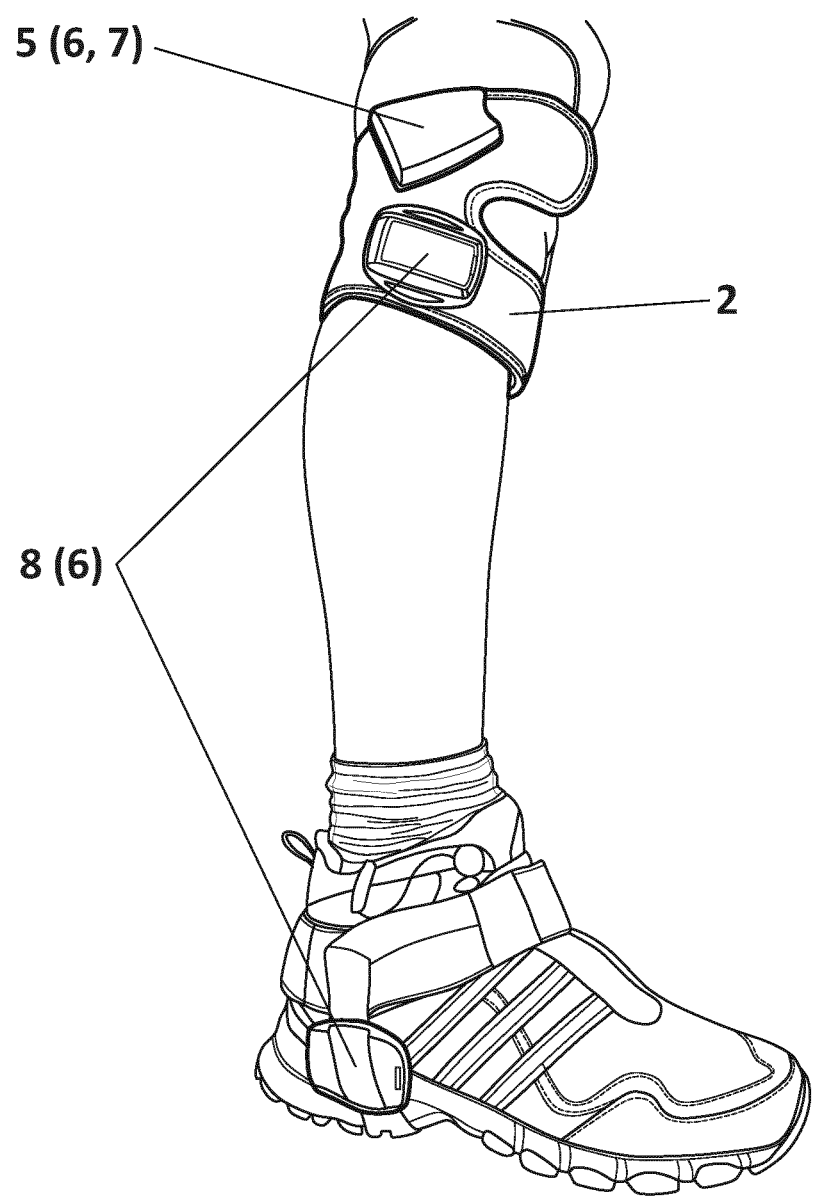
FIG. 3 illustrates the use of the multi-pad stimulation system during walking.

The FES system 1 also comprises at least one sensor unit 8 that is preferably placed on the foot. In an alternative embodiment, the sensor unit 8 is placed on the user's leg (or shank), preferably on the garment 2. FIG. 3 shows both possible implementations of the sensor unit 8. Non-limiting examples of sensor unit 8 are inertial sensors, such as inertial MEMS sensors, accelerometers and gyroscopes. The sensor unit 8 is preferably an inertial measurement unit (IMU). At least one sensor 8 is configured to, in use of the system, measure information during movement (during walking) and transmit sensor signals indicative of the movement to the stimulation and signal processing unit 6. These signals permit the control means 5 to calculate the foot trajectory and therefore the gait phase when the user is walking. The sensor 8 placed on the user's leg or shank (instead of on the user's foot) permits to detect foot and leg (or shank) trajectories. Since dynamic activation of the foot dorsiflexion can be detected at the shank, this signal can be used as means to measure quality of gait. The sensor 8 is preferably located on the foot because the data measured by the sensor placed on the leg or shank have normally inferior performance.

FIG. 3 shows one IMU sensor 8 on the user's foot. Preferably, a 6 degrees-of-freedom IMU is used, having 3 accelerometers and 3 gyroscopes, to obtain automatically the orientation of the sensor placed on the foot without requiring precise instructions on how to position it. In order to obtain the orientation of the sensor 8 an automated algorithm exploits moments of stance or gait during which the sensor is stationary. The sensor stationary state is determined as periods when the vector sum of gyro signals is close to ~0 and the vector sum of accelerometer signals is close to ~1 g, which is given by gravitation. During these periods the direction of the gravitational force can be determined (−z). The main direction of the leg during swing phase determines the sagital plane (with direction in x). The vector product of x and z determines the direction of inversion (y) and eversion (−y) of the foot. For optimization of dorsiflexion, the angular velocity around the y axis is analyzed and optimized. For eversion and inversion, the angular velocity around the z-axis is analyzed and optimized. This same description of the sensor 8 located on the foot applies to the sensor 8 when located on the leg or shank.

The main approach for characterization of foot movement for determination of the gait phases without knowing the exact position or orientation of sensor 8 is to use the NORM of angular velocity vector obtained from the 3-axis gyroscope. The NORM of the angular velocities obtained from the gyroscopes in x, y, and z direction is defined as sqrt $(x^2+y^2+z^2)$. This signal serves to determine the gait phases during the gait cycle and is from now on referred to as gyro signal.

FIG. 3 illustrates the use of the multi-pad stimulation system during walking. As explained next, the stimulator 6 is configured for receiving the signals captured by the sensor 8 for calculating the foot trajectory from the sensor signals, for detecting the gait phase from the foot trajectory and for modifying the stimulation patterns during walking. As already indicated, part of the control means (in particular at least part of the stimulation and signal processing unit 6, also referred to as a stimulator 6 or stimulating means) can be located at the sensor 8 (for example in a microprocessor) located either on the leg (shank) or on the foot. The stimulator 6 can be located alternatively at the housing 5 located on the garment 2. The main aim of this algorithm is to evaluate contributions of each stimulation pattern to a desired foot movement based only on the foot angular velocity signal in the saggital plane. The algorithm executes modifications in the stimulation pattern only when stability of a patient and trajectories of the foot are not compromised during walking by modifying the stimulation pattern and observing foot response (angular velocity). Such periods where modified stimulation patterns can be tested are during stance phase and during initial and towards end of the swing phase where the foot clearance is sufficient not to cause stumbling or disturbance on foot placement. If the stimulator 6 is in the housing 5, signals from sensor 8 are acquired and transferred to the stimulator using a wireless protocol; both, stimulator and IMU units are preferably equipped with wireless modules. If the stimulator 6 is in the sensor 8, there is no need of wireless transmission of the measurements. Based on signals obtained from the sensor 8, control and parameter modifications are executed. If the data acquired by the sensor 8 are processed in a microprocessor in the sensor unit 8, then the preprocessed or fully processed data can be transferred wirelessly to the remaining control means located in the housing 5. Like that, the amount of transferred data can be kept smaller. Examples of such processed data are determined triggers of gait phases as stance, lift-off, swing, heel strike, or other typical occurrences during gait. Actual limb angles with respect to the determined x,y,z-axes can also be calculated.

One stimulation pattern comprises a set of active pads within the multi-pad electrode, wherein each active pad is given appropriate stimulation pulse amplitude, frequency and pulse width. Each stimulation pattern also comprises specific time delays between successive pad activations. The system and method for correction of drop-foot permit the real-time optimization of the stimulation patterns produced by the multi-layer device 3, and therefore improve and maintain quality of the assisted movement. In other words, the system and method, based on the information captured by the sensor 8 positioned on a paretic (or impaired) leg of a patient, are able to modify the stimulation pattern during walking. This is achieved by a method implementing a fully automated procedure.

Figure 7:
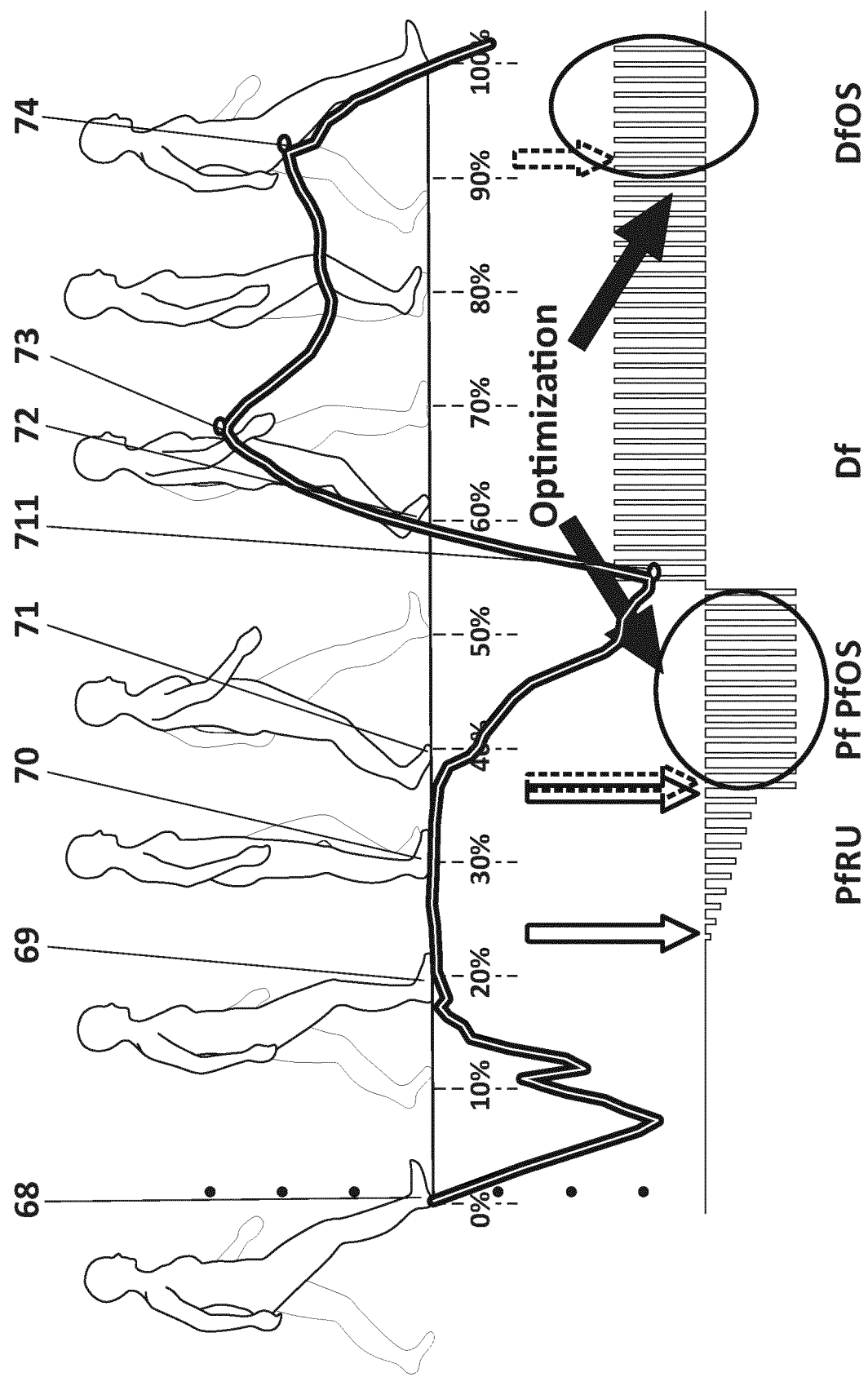
FIG. 7 represents the different gait phases of a walking user and the stimulation protocol associated to the different gait phases. It also shows the foot trajectory resulting from the inventive optimization procedure.

During use of the FES device 1 and execution of the method for the correction of drop-foot, the main goal is the production of functional foot movement. Functional foot movement is achieved when two conditions are fulfilled: when a strong plantar flexion (ankle extension) in the push-off gait phase for forward propelling of the body is produced (illustrated for example in FIG. 7, between reference numbers 71 and 72) and when a confident dorsiflexion (ankle flexion) in swing phase of gait for foot ground clearance is produced (illustrated for example in FIG. 7, between reference numbers 73 and 68). However, a functional gait can already be achieved when a confident dorsiflexion is produced. The aim of the drop-foot device and method is to achieve and maintain desired foot movement throughout use of the device. The evaluation of the stimulation results is done using the sensor 8 positioned on the affected foot of the user. The sensor 8 measures information while the user walks and transmits sensor signals indicative of the movement. From this signals, the foot trajectory is estimated. The foot trajectory is essential for detecting the gait phase. FIG. 7 represents the different gait phases of a walking user.

Figure 8:
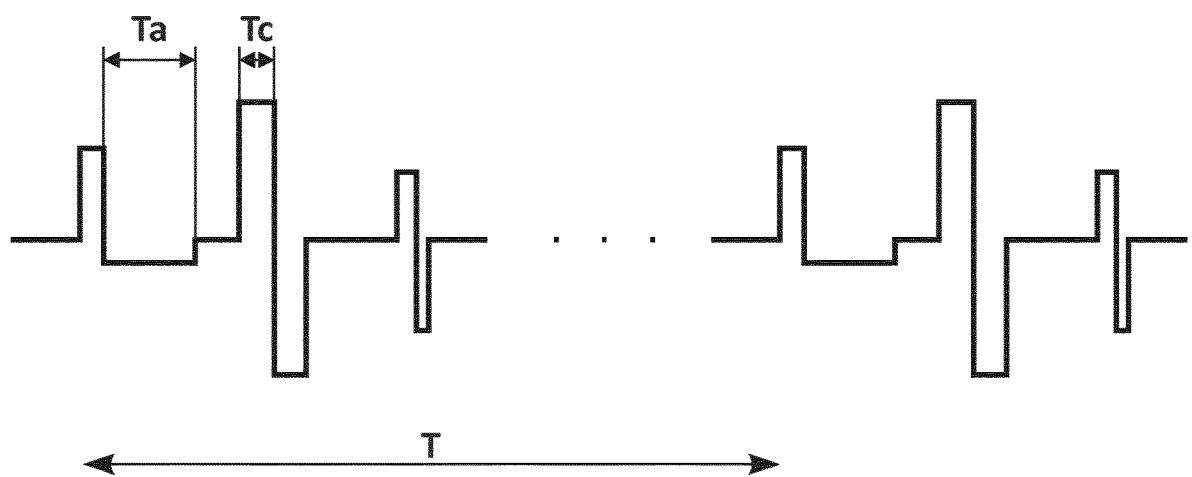
FIG. 8 shows an exemplary pattern of stimulation pulses delivered through the multi-pad electrodes.

In order to produce defined movements, single or synergistic muscle contractions need to be generated. These muscle contractions are generated by employing different stimulation patterns based on the discrete activation (or deactivation) of pads or electrodes 315 within a multi-pad electrode layer 31, by choosing the appropriate amplitude and width of the pulses applied to each electrode 315 in the stimulation and by choosing the appropriate time delays between successive pad (electrode) activations. All the possible combinations of the aforementioned parameters for optimally activating the multi-pad electrodes require complex control algorithms. FIG. 8 shows an exemplary pattern of stimulation pulses delivered through the multi-pad electrodes 315, wherein T is the period of cyclic repetitions of pads activation, Tc is the duration of the cathodic pulse and Ta is the duration of the anodic pulse (charge compensating pulse).

Each foot movement, and in particular the dorsiflexion and the plantar flexion, is associated with at least one stimulation pattern. The optimal position of the stimulation pads changes not only from user to user, but also for one same user in different stimulation sessions, and even in a single session, due to beginning of muscle fatigue or to a change of the skin-electrode interface and the distance of the electrode to the stimulated excitable tissues. For this reason, it is necessary that the FES system has the ability to adapt during use. The method associated to the FES system 1 optimizes in real-time the stimulation pattern produced by the multi-pad based device 3. The quality of the assisted movement provided by the system is thus improved and maintained. In particular, using feedback information obtained by the at least one sensor 8. The currently designated stimulation patterns are modified for achieving optimal plantar flexion and optimal dorsiflexion during gait. In a preferred embodiment, the stimulation protocol is designed as an event-driven state machine having state transitions based on inputs from sensors and timers (hardware modules inside the processor located in the housing 5 or in the sensor unit 8).

The method for optimizing the stimulation pattern:
(1) handles gait phase detection for initiating specific stimulation patterns, as explained in relation to FIG. 4;
(2) tracks foot movement for quality of gait evaluation, as explained in relation to FIG. 6; and
(3) executes, if necessary, a subroutine for stimulation pattern modification, which occurs in specified periods or time windows. This is explained in FIG. 5.

With respect to (1) handling gait phase detection for initiating specific stimulation patterns, stimulation patterns are cyclically executed as state machine outputs. The inputs for the state machine are: a) current state (for example, push-off gait phase), b) sensor signal shape in previous n points; a signal shape representing the angular velocity is the curve shown together with the gait cycle in FIG. 7; as the digitalization of sensors data is done in discrete time intervals (sampling time), the expression "previous n points" refers to n samples of sensors output preceding the last available sample; and c) the time elapsed from last detected event; event is a term that describes the characteristic predefined moment in cadence associated to the observation of foot movement (by sensor 8). These points are chosen as they are correlated to gait phase transitions (e.g. angular velocity exceeding negative threshold after period of rest is correlated with heel off . . . ).

Figure 4:
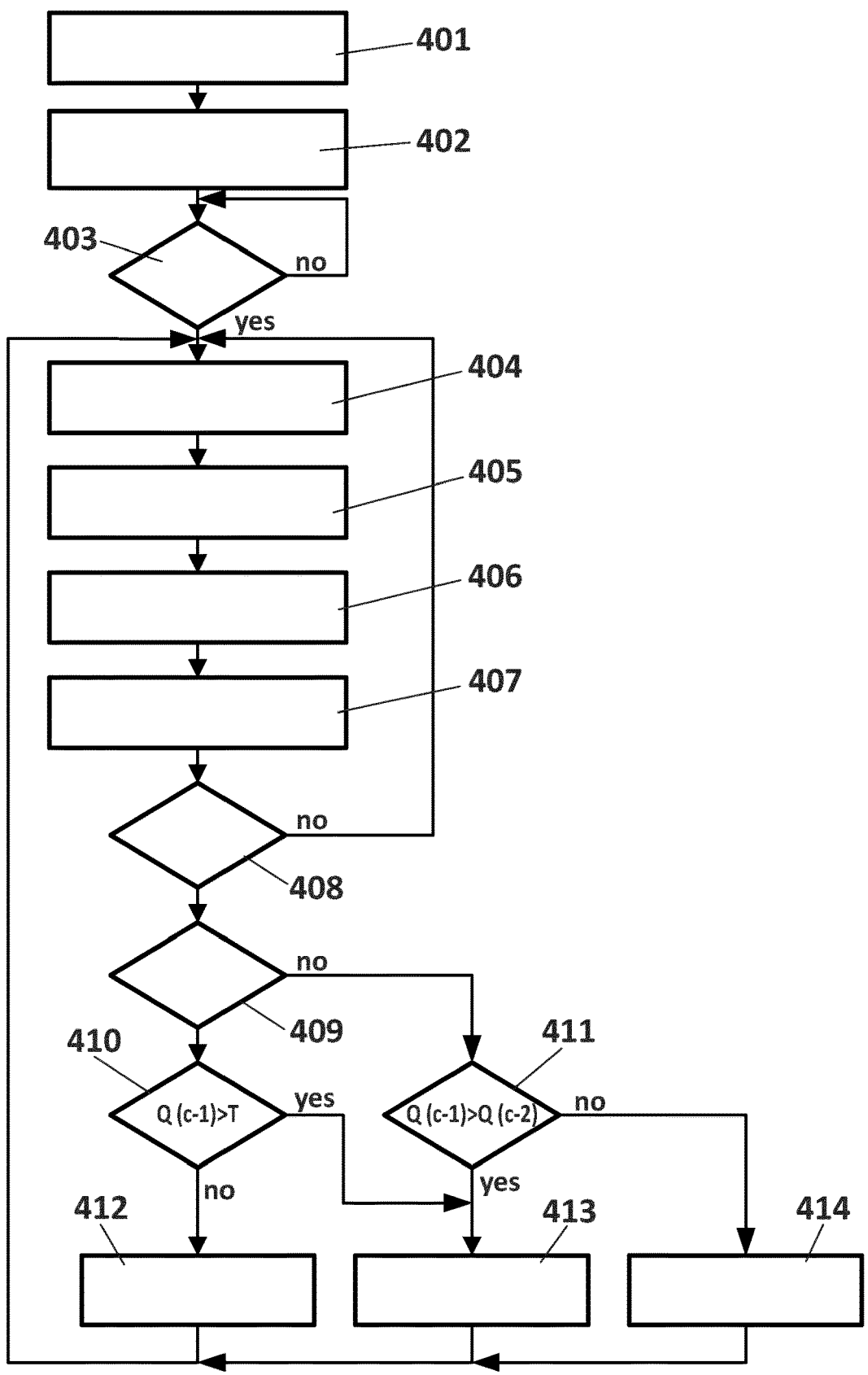
FIG. 4 illustrates a flowchart showing the method for assisted walking associated to the system of the invention.

FIG. 4 is a flowchart showing the method associated to the system of the invention. First (block 401), the stimulation system is initialized. Next (block 402), the stimulation parameters from a previous session are loaded. Stimulation parameters are stimulation patterns for dorsiflexion and plantar flexion. One stimulation pattern comprises a set of active pads within the multi-pad electrode, with appropriate stimulation pulse amplitudes and widths for each pad and time delays between successive pad activations. Then, it is possible to start the stimulation protocol (block 403) or not. If it is decided to start it (if "yes"), a stage (block 404) of acquisition of data from sensors and of values from timers, as well as data logging, is carried out. Timers are comprised in the processor within the housing 5 or within the sensor unit 8. The purpose of timers is to measure elapsed times from the last detected event in order to impose time constrains in automated decision making. Next, it is determined in which phase the gait cycle is (block 405). Decision is made using information of the current gait phase, signal "shape" and value of timer since last detected event. The process of gate phase detection based on characteristic events is repeated consecutively. Right after, a quality (Q) index for the current gait phase is calculated (block 406). The quality index is calculated using a mathematical function which is part of the automated algorithm running on the processor of the stimulator 6. Depending on the current gait phase (dorsiflexion or plantar flexion), a quality index for dorsiflexion Qd or a quality index for plantar flexion Qp are calculated and their values are derived from the correlation between the real foot trajectory (corresponding angular velocity) and the superimposed idealized foot trajectory (corresponding angular velocity). If present (because they are optional), user commands are decoded (block 407). The user can initiate a stimulation, indicate that a stimulation is painful or stop the automated algorithm by manually controlling the stimulator 6 or through a user application installed on a phone, tablet, etc. If present, this command has high priority and it is checked with each sensor sampling (for example, ~100 times a second).

Next, it is determined whether there is a change in the phase of the gait or not (block 408). If the phase of the gait has not changed (if "not"), the method goes back to the stage of acquisition of data from sensors and of values from timers, as well as data logging (block 404). If the phase of the gait has changed (if "yes"), it is checked whether an optimization phase is required or not (block 409). If dorsiflexion is the next phase and Qd of last step is below a certain threshold, optimization will be initiated. A similar procedure is applied for plantar flexion. The threshold is a dynamic characteristic for each patient, and is therefore adjustable to the patient's condition.

The quality index Q is a vector and the values of Qd or Qp are derived from Q depending on gait phase, where Qp is derived for plantar flexion and Qd for dorsiflexion. When the processor in the stimulator 6 enters one of the Optimization phases (PfOS or DfOS) and the quality index Q during the last phase (dorsiflexion for DfOS and plantar flexion for PfOS) is above a certain threshold, the algorithm does not enter the modification subroutine; instead, it uses the same pattern that was used during one of the last two steps. If the quality index Q is below a certain threshold, the algorithm runs a subroutine for the modification of the stimulation pattern (block 412). For dorsiflexion, based on Qd factors of the last two steps it will use a new pattern with better Qd (blocks 413 and 414). Entering Pf or PfOS is decided if during last plantar flexion Qp was above or below threshold.

With respect to (2) tracking of the foot trajectory, this task is done for evaluation of the generated movement. Based on a predefined, idealized trajectory (angular velocity profile), the deviation ε of a current step from that predefined trajectory is calculated.

This is done by applying a mathematical function on the samples captured from the sensor 8. Taking into account the deviation of individual samples from the idealized curve, the function returns a single value, which represents the Q factor of that foot movement. The algorithm automatically calculates the quality of gait. This is divided in two subcategories: The quality of plantar flexion and the quality of dorsiflexion. If quality of any of these categories is below a certain threshold, the algorithm initiates a subroutine (3) for stimulation pattern modification, with the objective of increasing the quality factor.

FIG. 11 shows an example of the execution of the algorithm for the modification of the stimulation pattern. For each stimulation pattern (on the left), a P table (pattern probability table, on the right) has values which represent the probability that the activation of the corresponding pad within the multi-pad electrode will contribute to generating a desired foot movement (dorsiflexion or plantar flexion). In fact, the P table comprises two tables Pd and Pt, for dorsiflexion and plantar flexion. P0 is "a priori" P table. It is the starting point for the modification of the stimulation pattern in the main optimization algorithm. During the optimization stage, the P table is modified based on the applied stimulation pattern and the produced quality of movement (Q).

Figure 10:
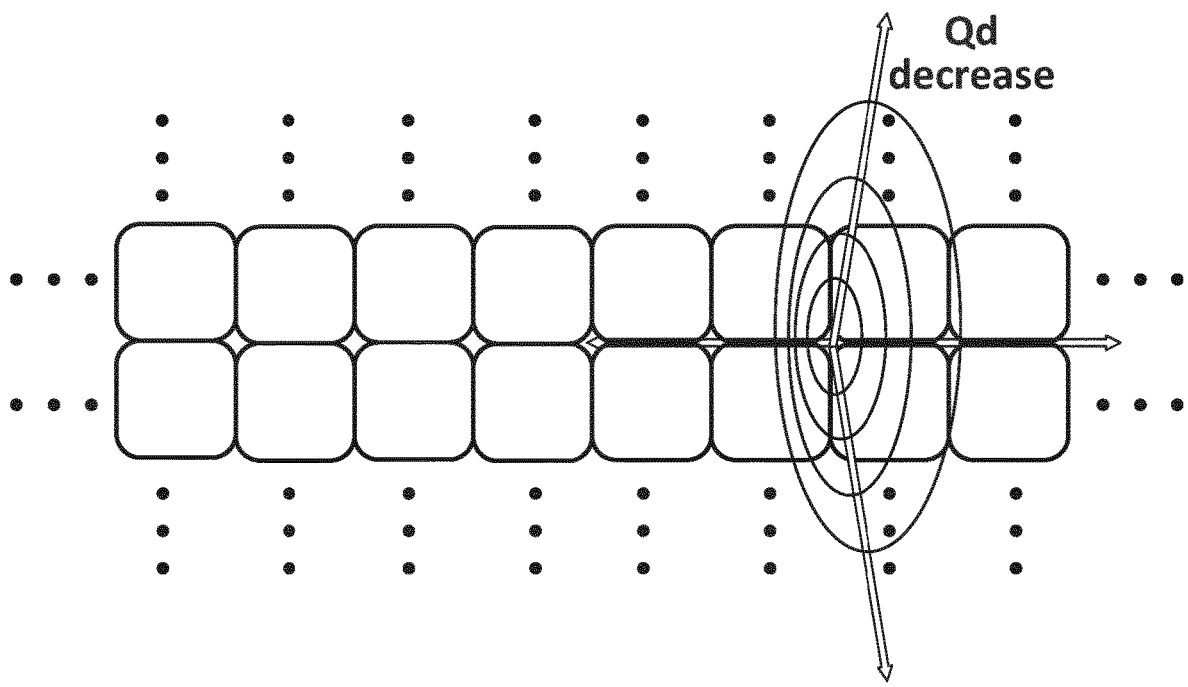
FIG. 10 shows a "a priori" P0 factor for dorsiflexion.

The algorithm for P factor recalculation converges to stable state from an initial (a priori) P0 factor table. The initial P0 factor table is based on statistical analysis of subjects involved in functional use of the drop-foot stimulation system or the P value used last time before the system was turned off. FIG. 10 shows a "a priori" P0 factor for dorsiflexion. It is a probability plot. It is made using a large number of optimization outcomes during user trials for producing desired dorsiflexion. FIG. 10 provides preferred pads at the beginning of the assisted walking (start of the protocol). Based on this graph, the algorithm determines which pads are going to be activated in order to raise Qd factor. This reasoning applies similarly to the Qp.

Figure 6:
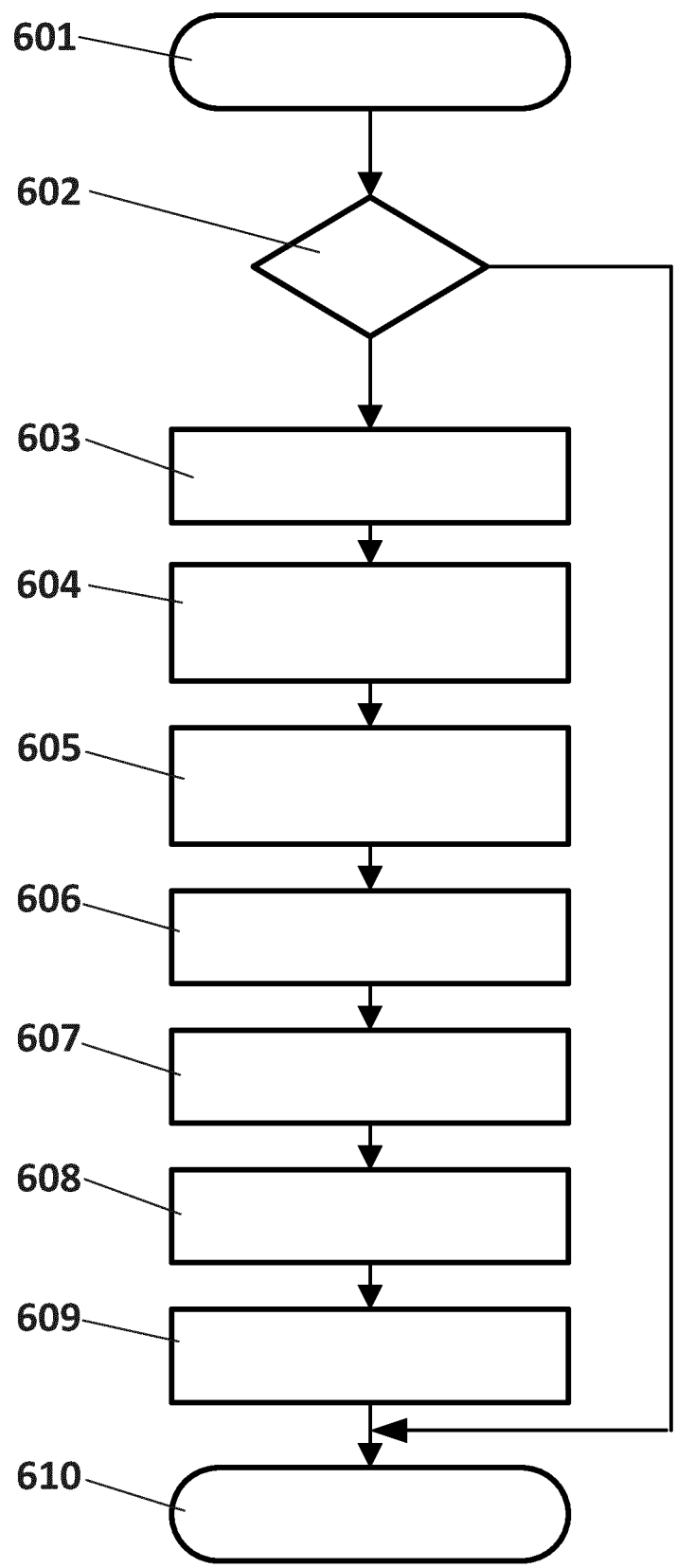
FIG. 6 illustrates a flowchart showing the method for P factor calculation.

FIG. 6 illustrates a flowchart showing the method for P factor calculation. First (block 601) the calculation of the P table is initialized. Next (block 602), based on a detected event it is decided to start an optimization phase or not. If it is decided to start it (if "yes"), the initial P0 table (a priori) for all pads is loaded from memory (block 603). Next, vector of recorded movements during the last optimization phase are loaded (block 604). Afterwards, the list of pads which were stimulated in the last optimization phase is loaded (block 605). Right after, the deviated trajectory (ε) from a idealized trajectory is calculated (block 606). Then, a quality function for the selected pads is applied (block 607). Next, the P factors for the selected pads are modified based on the quality function (block 608). The P table and the deviated trajectory (ε) are then saved (block 609) and the algorithm is returned (block 610).

Referring back to the illustration of the algorithm for the modification of the stimulation pattern of FIG. 11, in which a Qd threshold is defined (for example, Qd=60), during the first step, the stimulation pattern is derived from a priori P0 table (as shown in FIG. 11). The stimulation pattern is formed by (in the example) 2 active pads with largest values in P0 table, with predefined initial current amplitudes. After dorsiflexion, Qd is calculated based on the deviation of the foot trajectory from the idealized foot movement. Based on the achieved Qd, a next pattern is calculated. The first modification in the pattern is an increase in the stimulation amplitude, which results in stimulation pattern 1 (step 1 in FIG. 11). After the end of dorsiflexion, Qd is calculated again. As the increase of Qd is small compared to the threshold, the values of the active pads in P table are decreased, and increased in the still untested neighboring pads. If the Qd is still lower than the Qd threshold, the algorithm for the modification of the stimulation pattern is initiated. If the favorable pads from P table are still the same, the current amplitudes on the active pads are increased (pattern 3) (step 3 in FIG. 11). After dorsiflexion, Qd is calculated (block 607 in FIG. 6) based on the deviation of foot trajectory from the idealized foot movement (block 606). If the absolute value of the calculated Qd is low, the P table is modified (block 608 in FIG. 6) in such way that the P values of the active pads are further decreased. When the value of the P table for an inactive pad becomes greater than that of an active one, a new pad with its current set to the lowest threshold is automatically activated. In step 4 of FIG. 11, an increase of Qd is shown, which results in an increase of the P value of the newly activated pad. This also implies an increase of the stimulation current on that pad while the current on the pad with decreasing P value is decreased. Again, in the last step (step 5 in FIG. 11), Qd is calculated, which confirms the increasing trend. The P value of the pad with larger contribution to the Qd increase is also increased, while P values for other active pads are decreased and P values of untested pads, neighboring the preferred pad, also increase. This favors a new inactive pad over one active one having small P value. During the last step (step 5 in FIG. 11), the Qd value exceeds the quality threshold, making the last stimulation pattern optimal.

Figure 5:
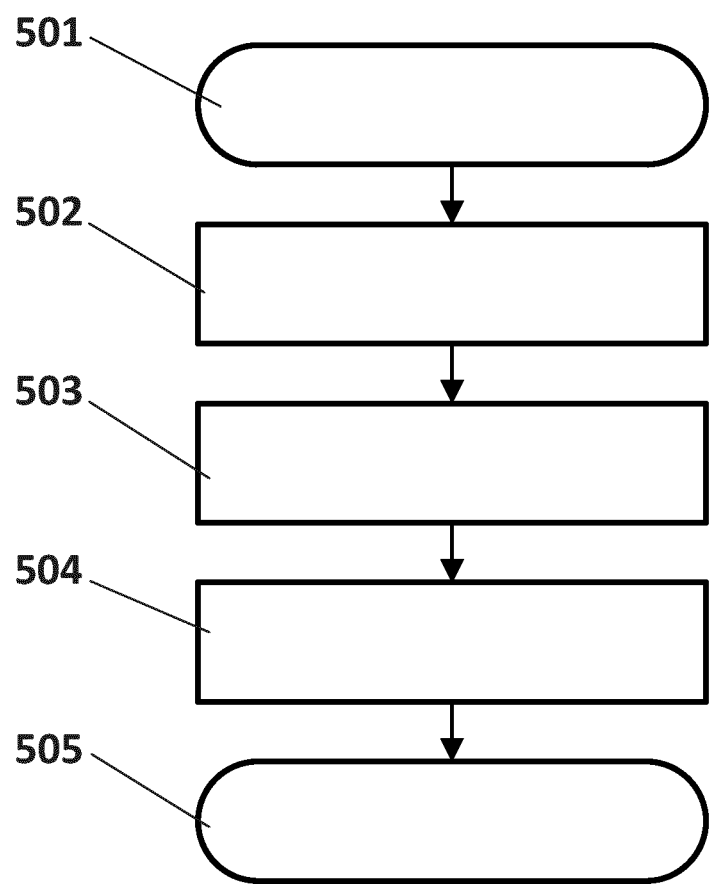
FIG. 5 illustrates a flowchart showing the modification of the stimulation pattern.

FIG. 5 is a flowchart showing the modification of the stimulation pattern. First (block 501) the modification of the stimulation pattern is initialized. Next (block 502), the stimulation pattern is loaded from memory. Then the stimulation amplitude of the pad with lowest value within P is decremented. Next, the stimulation amplitude of the pad with highest P value is incremented.

The subroutine (3) for modifying the stimulation pattern is executed in predefined time windows (periods) during which safety of a patient is not compromised. These periods are:

(3.1) For modification of the stimulation pattern in relation to the plantar flexion (because the quality of the plantar flexion is below a threshold): during push-off stage, between heel off and swing phase, wherein the gait event is defined as a point with local maximum of angular velocity (P maximum 711 in FIG. 7). The "heel off" is defined as the moment in time when the heel is totally lifted from the floor. After onset of stimulation, certain time delay is present before foot movement can be observed (50-100 ms). As push off duration is comparable with muscle reaction delay, the whole push off is designated as modification period. The modification procedure is initiated if the plantar flexion of the last step had Qp factor below threshold.

The point of P maximum can be estimated within an adaptable time window after heel off. If this maximum doesn't occur in the specified time window, time constrains will force initiation of dorsiflexion. This stage is illustrated in FIG. 7 and referred to as period between points 71 and 72 in this figure. The heel off event is a time instant and represents the transition from stance state and push off (plantar flexion) stage, where these two stages are continuous (not instantaneous). The heel off event is detected during stance state (immediately after) when angular velocity (gyro signal) exceeds a threshold of 20% of maximum negative angular velocity of previous gait cycles. The algorithm takes into account the 2 previous steps in order to modify all thresholds. After satisfying one of these conditions, detection of a P maximum in n points is enabled. N points are the last n acquired samples from sensor 8. The update of thresholds and time constraints happens at the end of the gait cycle when a global maximum is extracted. The main purpose of these constraints is to prevent false detections from occurring. Updated values are preferably calculated using k last steps as median values. To emphasize again the processing and determination of the Q and P values, they can either be done in the processing means of the housing 5 or in the processing means of the sensor unit 8, when the amount of transmitted data needs to be kept small. In this case the Q and P values are calculated in the processing means of the sensor unit 8 and wirelessly transmitted to the housing 5.

During this short period, illustrated in FIG. 7 between references 71 and 72, the patient is pushing forward, and if the modification of the stimulation pattern produced unwanted foot movement, it would influence only kinematic aspects of gait including speed, symmetry and cadence, but would not cause potential instability. The next stage of modification of the stimulation pattern is the one related to the dorsiflexion (3.2).

Figure 9:
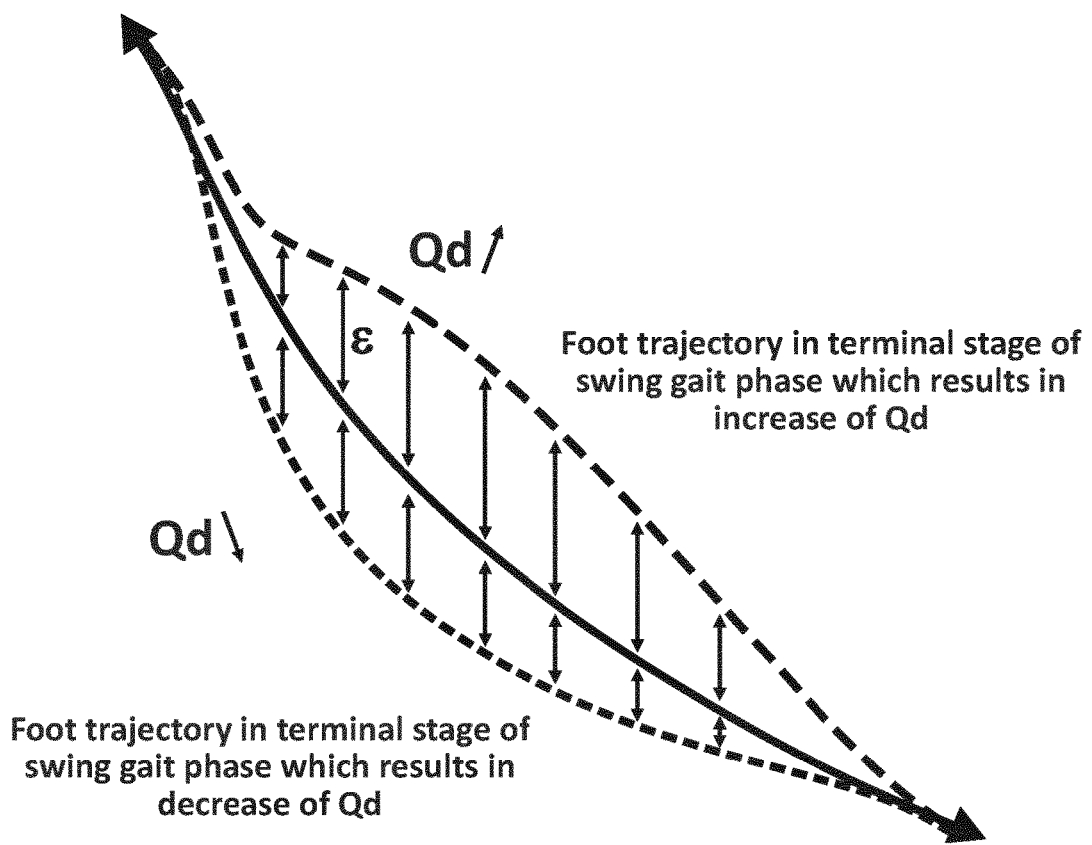
FIG. 9 illustrates the calculation of the deviation in the measured trajectory with respect to a predefined trajectory during DfOS.

(3.2) For testing the modifications of the stimulation pattern in relation to the dorsiflexion test stimulation patterns are applied during terminal stage of swing, starting at a point of 50% of maximal positive angular velocity of swing 74 and heel contact 68, where maximal positive angular velocity is 73. This period is illustrated in FIG. 7. During this short part of the swing phase, the foot of the patient has passed the point of minimal foot clearance. Based on a stimulation twitch generated by the modification of stimulation pattern, the algorithm assesses if the modification in the stimulation pattern is increasing or decreasing dorsiflexion strength. A muscle twitch is the result of a perturbation of the stimulation pattern. The main purpose of the twitch is to produce differentiation between an applied pattern and a modified pattern. The evaluation is based on the actual trajectory shape compared to the predefined, goal trajectory. In FIG. 9, the middle line is a predefined trajectory, while upper and lower lines represent trajectories that lead to increase or decrease of Qd.

The stimulation protocol comprises the following stimulations, which are illustrated in FIG. 7 in relation to the different gait phases during walking. FIG. 7 also shows the foot trajectory resulting from the inventive optimization procedure. The stimulations for a whole gait cycle are:

(1) Ramp-up stimulation for gradual increase of force in muscles involved in plantar flexion (PfRU). The event for triggering this stimulation stage is based on the time delay after detection of heel strike on the floor (reference 69 in FIG. 7). It is triggered inside a defined time window with fixed start and end time in respect to the flat foot detection. The start time can be 0 and in that case ramp is starting after detection of flat foot on the ground (gyro~0). The PfRU is time limited and if a heel-off event does not occur in a predefined time window, the stimulation is switched off. This stimulation stage occurs approximately when the gait cycle is between its 20% and its 30% (references 69 70 in FIG. 7).

The starting stimulation pattern during this stimulation stage is the previously optimized stimulation pattern for plantar flexion. The increases of the individual amplitudes are defined by the ramp time and by final pulse amplitudes values, where final pulse values are defined as values of Pf pattern. Similar activation pattern is present in able-body persons during stance phase of gait.

(2) The stimulation called Plantar flexion optimization state (PfOS) is initiated during push-off gait phase. The event for triggering PfOS is when the heel first moves off the floor, which is detected using foot angular velocity. When the value registered by a sensor 8 exceeds a set threshold, the push-off phase is detected and stimulation enters in its PfOS stage. This is represented in FIG. 7, where it can be seen that this stimulating stage is triggered when the push-off gait phase starts (immediately after reference 69, when the PfRU stimulation stage has finished). This stimulation stage occurs approximately when the gait cycle is between its 30% and its 40% (references 70 71 in FIG. 7).

During this PfOS stage, the stimulation pattern is modified for plantar flexion, based on a plantar flexion quality function (Qp). Qp is a derived mathematical function. Taking into account the deviation of individual samples from the artificial curve, this function returns a single value which represents Qp factor. It is a predefined function. The effect of the modified stimulation pattern is evaluated using the deviation of the foot trajectory from a reference trajectory. Such deviation is obtained from the information captured by sensor 8 (FIG. 3). Based on the pattern modification and on the elicited trajectory, Qp factors are recalculated. If the previous PfOS stimulation produced plantar flexion above the defined quality threshold (this is evaluated using the deviation of the foot trajectory from a reference trajectory), the next PfOS stimulation will use the same stimulation pattern (without pattern modification).

(3) The stimulation of dorsiflexors occurs during swing phase of gait (Df). The stimulation pattern during this stimulation stage is the dorsiflexion pattern, optimized during the last dorsiflexion optimization state (DfOS), which comes in the gait cycle afterwards, as illustrated in FIG. 7.

Taking into account the time delay between onset of the stimulation and the elicited muscle force, the stimulation of dorsiflexion is initiated at the toe off (reference 711 in FIG. 7). The event used for initiating this stimulation (Df) is the local maximum negative angular velocity during early swing phase. Muscle activation for dorsiflexion occurs between its 60% and its 90% (100% if DfOS is not necessary) (between references 72 and 74 in FIG. 7).

(4) The last stimulation, called dorsiflexion optimization state (DfOS) is initiated in the terminal stage of swing phase (previous stimulation pattern). This stimulation state is executed if Qd of the last step is below threshold. The event for triggering this state is defined as the 50% of maximum of the foot angular velocity.

During this gait phase, the foot has left the minimum foot clearance and perturbation in the stimulation pattern cannot induce fall due stumbling. So, during DfOS, the stimulation pattern is modified for dorsiflexion, based on a dorsiflexion quality function (Qd). Qd also takes into account inversion and eversion of the foot and optimizes by minimizing both inversion and eversion of the foot. The effect of the modified stimulation pattern is evaluated using the deviation of the foot trajectory from the reference trajectory. Based on the pattern modification and on the elicited trajectory (obtained through the sensor 8), Qd factors are recalculated. FIG. 9 illustrates the calculation of the deviation ($\epsilon$) in the measured trajectory with respect to a predefined trajectory during DfOS. The procedure of DfOS stimulation can be applied independently of the Q factor dropping down below a certain threshold, since the change of the gait quality at this late phase of the swing does not influence the safety of gait. Therefore, the optimization of dorsiflexion can be performed at any step. The resulting P table can be continuously optimized and in case of a drop of Qd below a certain threshold a better stimulation pattern is ultimately at disposal.

During any of the stimulation stages, if steady state is detected, the system skips to the rest (no stimulation) stage.

If one of the stages is not properly discriminated by the defined event, time constraints force the occurrence of the next stage; in this situation, the modification states have lower priority compared with Df state.

The set of stimulation parameters, obtained as a result of the optimization procedure, is defined for each active pad 315 individually, and includes pulse width, pulse amplitude, shape of compensation (which represents the type pf the stimulation pulse) and time delay between activation of subsequent pads. The modification of the stimulation patterns include increase/decrease of the stimulation parameters (pulse amplitude, pulse width and frequency) and changing the selected set of active pads based on the functionality of proximal pads determined during the optimization procedure.

In sum, the device and method of this invention provides important advantages with respect to conventional ones. For example, with respect to the device disclosed in WO2011/079866A1, the present device and method are capable of calculating a foot trajectory from the sensor signals, detecting gait phase from the foot trajectory, evaluating the quality of gait from the foot trajectory and, if the quality of gait is below a certain threshold, modifying the stimulation pattern applied to the electrodes. What is more, within the gait cycle at specific time instances (e.g. end of swing phase) new electrode activation configurations (different subsets of pads) are activated and analyzed with the sensor signals regarding the improved function. These new better activation means are tested with a short pulse train and the impulse response is analyzed. In case the quality of gait is below a certain threshold, the electrode activation configuration that has shown the best impulse response, replaces the previous configuration.

As apparent from the content of this description, the system offers a solution to the problem of positioning the stimulation electrodes such that an optimal movement is obtained. Furthermore, the system is capable of adjusting the stimulation parameters automatically. Besides, fatigue can be delayed through asynchronous, distributed stimulation. The stimulation becomes extremely selective, targeting precisely the needed nerves and muscles.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A functional electrical stimulation system (1) for correction of drop-foot, comprising:
   a device (3) configured to be placed on a paretic leg of a user, the device (3) being provided with a plurality of multi-pad electrodes (315) on one side (31), at least one of the electrodes (315) being configured to provide a stimulating electric signal on a point of the leg on which it is positioned, wherein said corresponding stimulating electric signals form a stimulation pattern;
   at least one sensor (8) configured to be positioned on either the paretic leg or corresponding foot of the user during use of the system (1), the sensor (8) being configured to, in use of the system, measure information during movement and emit sensor signals indicative thereof;
   means (6) for calculating a foot trajectory from the sensor signals, for detecting gait phase from the foot trajectory, for evaluating the quality of gait from the foot trajectory by calculating a deviation ($\epsilon$) of foot trajectory of a current step from a predefined foot trajectory and for, if the quality of gait is below a certain threshold, modifying the stimulation pattern either during push-off stage,. if the quality of plantar flexion is below the threshold, or during terminal stage if the quality of dorsiflexion is below the threshold, the modification including decrementing the stimulation amplitude of the electrical signal at the electrode of the multi-pad electrodes having a lowest amplitude value and incrementing the stimulation amplitude of the electrical signal at the electrode of the multi-pad electrodes having a highest amplitude value; and
   means (7) for selectively activating at least one of the electrodes (315) according to the modified stimulation pattern.

2. The system (1) of claim 1, wherein the means (7) for selectively activating at least one of the electrodes (315) according to the modified stimulation pattern comprises multiplexor means for discrete activation or deactivation of electrodes (325) and for adjusting at least one of the following parameters associated to each electrode: the amplitude of the pulse, the width of the pulse and the time delay between consecutive electrode activations.

3. The system (1) of claim 1, further comprising a garment (2) to which the device (3) is attached.

4. The system (1) of claim 1, wherein the sensor (8) comprises means for obtaining its own orientation based on the moments of stance of gait during which the sensor (8) is stationary.

5. The system (1) of claim 4, wherein the means for obtaining the sensor (8) orientation comprises a plurality of accelerometers and a plurality of gyroscopes.

6. The system (1) of claim 1, wherein the means (6) for calculating a foot trajectory from the sensor signals, for detecting gait phase from the foot trajectory, for evaluating the quality of gait from the foot trajectory and for, if the quality of gait is below a certain threshold, modifying the stimulation pattern, are at least partially located in the sensor (8).

7. The system (1) of claim 1, wherein the means (6) for calculating a foot trajectory from the sensor signals, for detecting gait phase from the foot trajectory, for evaluating the quality of gait from the foot trajectory and for, if the quality of gait is below a certain threshold, modifying the stimulation pattern, are at least partially located in a housing (5) located on the user's leg.

8. The system (1) of claim 1, further comprising means for wirelessly sending data obtained, preprocessed or processed at the sensor (8) to processing means in a different location.

* * * * *